United States Patent

Macher et al.

[11] Patent Number: 5,440,015
[45] Date of Patent: Aug. 8, 1995

[54] SELECTIN PEPTIDE MEDICAMENTS FOR TREATING DISEASE

[75] Inventors: Bruce A. Macher, Corte Madera; John B. Briggs, San Anselmo, both of Calif.

[73] Assignee: Glycomed Incorporated, Alameda, Calif.

[21] Appl. No.: 38,385

[22] Filed: Mar. 29, 1993

Related U.S. Application Data

[63] Continuation-in-part of Ser. No. 917,487, Jul. 21, 1992, abandoned.

[51] Int. Cl.⁶ .................. A61K 38/00; C07K 5/00; C07K 7/00; C07K 17/00
[52] U.S. Cl. ............................... 530/329; 530/328
[58] Field of Search .................. 530/328, 329, 324; 514/12, 16, 17

[56] References Cited

FOREIGN PATENT DOCUMENTS

| | | | |
|---|---|---|---|
| 9005786 | 5/1990 | WIPO | C12P 21/00 |
| WO9201718 | 2/1992 | WIPO | |
| WO9213887 | 8/1992 | WIPO | |
| WO9220708 | 11/1992 | WIPO | |
| WO9305070 | 3/1993 | WIPO | |
| WO93/08211 | 4/1993 | WIPO | C07K 5/06 |
| WO93/24526 | 12/1993 | WIPO | C07K 7/06 |
| WO93/24527 | 12/1993 | WIPO | C07K 7/06 |
| WO94/04568 | 3/1994 | WIPO | C07K 15/00 |
| WO94/05269 | 3/1994 | WIPO | A61K 31/00 |
| WO94/05310 | 3/1994 | WIPO | A61K 37/00 |
| WO94/05314 | 3/1994 | WIPO | A61K 37/02 |

OTHER PUBLICATIONS

Geng et al., *Journal of Biological Chemistry* (1992) 267(28):19846–19853.
Geng et al., *Journal of Biological Chemistry* (1991) 266(33):22313–22318.
Johnston et al., *Cell*, vol. 56, (1989) pp. 1033–1049.
Bevilacqua et al., *Science*, vol. 243 pp. 1160–1165, Mar. 1989.

*Primary Examiner*—Jill Warden
*Assistant Examiner*—A. M. Davenport
*Attorney, Agent, or Firm*—Gregory J. Giotta; Vandana Date

[57] ABSTRACT

Peptides are described and methods of using the peptides to treat or prevent disease which peptides are described by the formula:

SEQ. ID NO::

wherein X is an aromatic amino acid, and n is 1, 2, or 3; X' is either a non-polar or polar uncharged amino acid, and n' is 1, 2, or 3; X'' is a basic amino acid, and n'' is 1 or 2.

8 Claims, 2 Drawing Sheets

SELECTIN PEPTIDE MEDICAMENTS FOR TREATING DISEASE

CROSS-REFERENCE TO RELATED APPLICATION

This application is a continuation-in-part of U.S. patent application Ser. No. 07/917,487 filed 21 Jul. 1992 and now abandoned.

FIELD OF THE INVENTION

This invention is in the field of biochemistry/molecular biology with emphasis on the identification of peptides that are useful for treating or preventing disease arising from unwanted cell-cell adhesion.

BACKGROUND ART

It is now well established that cellular interactions are at least in part mediated by receptor/ligand interactions. One class of receptors is known to recognize the peptide sequence "RGD"; other receptors recognize carbohydrate ligands.

One class of receptors that recognize carbohydrate-based ligands mediates the adhesion of circulating neutrophils to stimulated vascular endothelium. This is a primary event of the inflammatory response and appears to be involved as well in allergic and autoimmune responses. Several receptors have been implicated in this interaction, including a family of putative lectins that includes gp90$^{MEL}$ (Leu8), ELAM-1, and GMP-140 (PADGEM) and (Gong, J. -G., et al., *Nature* (1990) 343:757; Johnston, G. I., et al., *Cell* (1989) 56:1033; Geoffrey, J. S., and Rosen, S. D., *J. Cell Biol.* (1989) 109:2463; Lasky, L. A., et al., *Cell* (1989) 56:1045). These lectins have been termed L-SELECTIN, E-SELECTIN, and P-SELECTIN.

E-SELECTIN is perhaps the best characterized of the three selectins. It is particularly interesting because of its transient expression on endothelial cells in response to IL-1 or TNF (Bevilacqua, M. P., et al., *Science* (1989) 243:1160). The time course of this induced expression (2-8 hours) suggests a role for this receptor in initial neutrophil extravasation in response to infection and injury. Furthermore, Bevilacqua et al. (see Bevilacqua, M. P., et al., *Proc. Natl. Acad. Sci. USA* (1987) 84:9238) have demonstrated that human neutrophils or HL-60 cells will adhere to COS cells transfected with a plasmid containing a cDNA encoding for the E-SELECTIN receptor. Information regarding the DNA sequences encoding for endothelial cell-leukocyte adhesion molecules are disclosed within PCT published application WO90/13300 published Nov. 15, 1990.

Recently, several different groups have published papers regarding the ligand for E-SELECTIN. Lowe et al., (1990) Cell, 63:475-484 reported a positive correlation between the E-SELECTIN dependent adhesion of HL-60 cell variants and transfected sell lines, with their expression of the sialyl Lewis x (sLex) oligosaccharide, NeuAc α2-3Gal-β1-4(Fuc α1-3)-GlcNAc. By transfecting cells with plasmids containing an α(1,3/1,4) fucosyltransferase, they were able to convert non-myeloid COS or CHO lines into sLex-positive cells that bind in an E-SELECTIN dependent manner. Attempts to block E-SELECTIN dependent adhesion using anti-sLex antibodies were uninterpretable due to the agglutination of the test cells by the antibody. They concluded that one or more members of a family of oligosaccharides consisting of sialylated, fucosylated, lactosaminoglycans are the ligands for the lectin domain of E-SELECTIN. Phillips et al., (1990) Science, 250:1130-1132 used antibodies with reported specificity for sLex to inhibit the E-SELECTIN dependent adhesion of HL-60 or LEC11 CHO cells to activated endothelial cells. Liposomes containing difucosylated glycolipids with terminal sLex structures inhibited adhesion, while those containing nonsialylated Lex structures were partially inhibitory. Walz et al., (1990) Science, 250:1132-1135 were able to inhibit the binding of a E-SELECTIN-IgG chimera to HL-60 cells with a monoclonal antibody directed against sLex or by glycoproteins with the sLex structure, but could not demonstrate inhibition with CD65 or CD15 antibodies. Both groups concluded that the sLex structure is the ligand for E-SELECTIN. U.S. patent application Ser. No. 07/683,458, filed 11 Apr. 1991 assigned to the present assignee and incorporated herein by reference discloses and claims the foregoing minimum tetrasaccharide structure and identifies the groups putatively interactive with the ELAM-1 receptor.

In contrast to E-SELECTIN, the properties of the ligands that bind to L-SELECTIN and P-SELECTIN are not as well worked out. L-SELECTIN appears to bind a sialic acid bearing ligand based on neuraminidase treatment of peripheral lymph node high endothelial venules which inhibits L-SELECTIN recognition. True et al., 1990, J. Cell Biol. 111, 2757-2764. Further, other studies using soluble L-SELECTIN in direct binding/inhibition assays suggests that certain carbohydrate moieties may be important ligand components including mannose and fucose, particularly when sulfated or phosphorylated. Imai et al., 1990 J. Cell Biol. 111, 1225-1232. More recent studies suggest that L-Selectin binds to sialyl Lewis X. Foxall, C., et al., (1992) J. Cell Biology, 117:895-902.

The ligand to P-SELECTIN is thought to have an epitope related to sialyl Lewis x. This conclusion is based on studies using antibody with this specificity that block P-SELECTIN mediated adhesion of HL-60 cells to activated platelets or COS cells that express P-SELECTIN. Larsen et al. (1990) Cell 63, 467-474. Other experiments have shown that the adhesion of HL-60 cells to P-SELECTIN transfected cells is blocked by the pentasaccharide isolated from milk that has the Lewis$^x$ epitope. Recently, P-Selectin has been shown to bind to sulfatides. Aruffo, A., et al. (1991) Cell, 67:35-44.

It has recently been shown that peptides derived from the selectin GMP-140, or P-SELECTIN, including peptides that span the following amino acids of the selectin 19-34, 54-72 and 66-89 interfere with the binding of neutrophils to GMP-140. PCT publication number, WO 92/01718, inventor Mcever, R.; PCT publication number, WO 92/20708, inventor Heavner, G. et al., J. Biol. Chem. 266:22313-22318 (1991), and J. Biol. Chem. 267:19846-19853(1992). It was suggested that these peptides would be useful as diagnostics and therapeutics. Because of the role of selectins in disease, particularly diseases involving unwanted cell-cell adhesion that occurs through selectin-ligand binding on defined cell types, the identification and isolation of novel ligands that would permit the regulation of such selectin-ligand binding is sorely needed.

OBJECTS OF THE INVENTION

The invention provides peptides that interfere with the binding of selectin ligands to their receptors and thus modulate the course of inflammation, cancer or other diseases by modulating cell-cell adhesion events. In this aspect, the invention is directed to peptides that have the formula:

SEQ ID NO:1 wherein X is an aromatic amino acid, n is 1,2, or 3; X' is a non-polar amino acid, n' is 1, 2, or 3; X" is a polar amino acid, and n" is 1 or 2.

A second object of the invention is the description of methods for treating or preventing disease by administering an effective amount of a peptide(s), alone or in combination, that have the formula:

SEQ ID NO:2

SEQ ID NO:3

SEQ ID NO:4, or

SEQ ID NO:5

A third object of the invention is the description of methods for treating or preventing disease by administering an effective amount of the peptides wherein the peptides are acetylated at the amino terminal end and-/or amidated at the carboxyl terminal end. The peptides may be modified to increase their in vivo residence circulation time, using, for example, polyethylene glycol or similar polymers well known in the art.

A fourth object of the invention is the description of antibody that binds to the peptides of formula 1-5, and methods of using the antibody to prevent or treat disease.

These and other objects of the invention will become apparent upon a full consideration of the following disclosure.

BRIEF DESCRIPTION OF THE DRAWINGS

Table 1 shows the extinction coefficients for certain peptides of the invention.

Table 2 shows the effects of certain peptides on inhibition of thioglycolate induced peritonitis in mice.

Table 3 shows the effects of certain peptides on inhibition of HUVEC cell binding to HL-60 cells.

DETAILED DESCRIPTION OF THE INVENTION

In describing the invention set forth below, reference is often made to certain scientific or patent publications. It is the intent that these publications, in their entirety, be incorporated into the instant patent.

The invention described herein is a family of peptides that can be used as medicaments or diagnostics for treating or diagnosing certain diseases. The peptides have the following formula:

SEQ ID NO:1 wherein X is an aromatic amino acid, and n is 1, 2, or 3; X' is either a non-polar or polar uncharged amino acid, and n' is 1, 2, or 3; X" is a basic amino acid, and n" is 1 or 2. Amino acids that have aromatic, non-polar, or polar uncharged characteristics are well known in the art. See Lehninger, A. L. Biochemistry (2nd, ed. Worth Publishers, Inc.) 1975, pages 73–75.

Preferred non-polar amino acids as used in the invention include: alanine, valine, leucine, isoleucine, proline, methionine. Polar uncharged amino acids include glycine, serine, threonine, asparagine and glutamine. Basic amino acids include lysine, arginine and histidine. Aromatic amino acids include phenylalanine, tryptophan, and tyrosine.

In some instances peptides made of D-amino acids will be preferred. For instance, since peptides made of D-amino acids are known to have enhanced in vivo stability, where peptide stability is a key consideration in treating a particular disease indication D-amino acid peptides will be preferred over the L-amino acid peptides.

In addition to the 20 common amino acids, other amino acids are known that can be synthesized using known synthetic techniques. An appropriate amino acid selected from this group may replace one or more of the common amino acids denoted in formula 1.

The peptides of formula 1 may be acetylated at the amino terminal end and/or amidated at the carboxyl terminal end.

The embodiment peptide has the following formula:

SEQ ID NO:2

The amino acid sequence shown in formula 2 is present in the P-SELECTIN, E-SELECTIN and L-SELECTIN lectin domains. The single letter code is used to denote the known amino acids.

A embodiment peptide is the peptide of formula 2 that is acetylated at the amino terminal end and amidated at the carboxyl terminal end.

With the above description of the invention in mind, methods of making and using the peptides will now be presented.

Synthesis of the Peptides

The peptides of the instant invention can be made using established techniques well known to the skilled practitioner of this art. For example, the peptides can be synthesized using the solid phase synthesis method described by J. Merrifield, J. Am. Chem. Soc. 85, 2149 (1964). The Merrifield method is used in U.S. Pat. No. 4,792,525, and in U.S. Pat. No. 4,244,946. Additional methods of synthesizing peptides are set forth in U.S. Pat. No. 4,305,872 and U.S. Pat. No. 4, 316,891.

Assays to Test Peptide Activity

In their most general form assays for identifying peptides that interfere with selectin ligand binding involve contacting the appropriate selectin, L-SELECTIN, E-SELECTIN, or P-SELECTIN, with an appropriate ligand in the presence of peptide, and measuring the degree to which the peptide inhibits selectin ligand binding.

Several assays are available to measure the capacity of a peptide to interfere with selectin ligand binding to L-SELECTIN, E-SELECTIN, or P-SELECTIN, and such assays are well known in the art. For example, both the selectin and the ligand may be in solution for a time sufficient for a complex to form consisting of the selectin and ligand, followed by separating the complex from uncomplexed selectin and ligand, and measuring the amount of complex formed. Alternatively, the amount of uncomplexed selectin or compound could be measured. The effect of an appropriate peptide on selectin ligand binding is readily ascertained by having the peptide present during the incubation period.

A second and assay format consist of immobilizing either the selectin or the putative ligand on a solid surface, and forming the selectin-ligand complex thereon by contacting the immobilized reagent with the non-immobilized reagent. The selectin-ligand complex is separated from uncomplexed reagents, and the amount of complex formed can be determined by measuring the amount of the non-immobilized reagent present in the complex. For example, the selectin ligand can be affixed to a microtiter well, followed by adding the desired selectin to the well and measuring the amount of selectin bound to the ligand. Hereto, the effect of an appropriate peptide on selectin ligand binding is readily ascertained by having the peptide present during the incubation period.

Yet another assay, is to affix a selectin to a microtiter well, and measure the degree to which a peptide of formula 1 interferes with the binding of cells that express a particular selectin ligand to the selectin. For example, peptides with inhibitory activity are those which inhibit binding of neutrophils and monocytes to P-selectin, or which inhibit leukocyte adhesion to endothelium that is mediated by E-selectin. This type of assay is utilized in the Example section to identify inhibitory peptides wherein HL-60 cell binding to P and E-SELECTIN is assayed. This type of assay is generally described by J. G. Geny et al, Nature 343:757–760, 1990. Cells utilized in the assay may be labelled with a variety of tracers, including fluorescent dyes. One such dye is BCECF-AM, or 2',7'-bis-(2-carboxyethyl)- 5- (and 6)-carboxy-fluorescein, acetoxy methyl ester, obtainable from Molecular Probes, Inc. Eugene, Oreg. (product number B-1150). See also, J. Cell Biol., 95, 189–196 (1982).

A variation of the above assay is to genetically engineer cells to express high levels of L-SELECTIN, E-SELECTIN, or P-SELECTIN on their surface, and to use the cells in lieu of purified selectin. Radiolabeled COS cells have been used in this type of assay, and can be transfected with cDNA that encodes for L-SELECTIN, E-SELECTIN or P-SELECTIN. After the cells have had a sufficient time to adhere to the ligand coated microtiter well, in the presence or absence of an appropriate peptide, non-adherent cells are removed and the number of adherent cells determined. The number of adherent cells reflects the capacity of the ligand to bind to the selectin. The effect of the peptide is readily measured by a decrease in the number of adherent cells. Representative of the application of this type of assay is the identification of E-SELECTIN ligands. For example, a complete cDNA for the ELAM-1 receptor was obtained by PCR starting with total RNA isolated from IL-1 stimulated human umbilical vein endothelium. The resulting cDNA was inserted into the CDM8 plasmid (see Aruffo, A., and Seed, B., Proc. Natl. Acad. Sci. USA (1987) 84:8573) and the plasmid amplified in E. coli. Plasmid DNA from individual colonies was isolated and used to transfect COS cells. Positive plasmids were selected by their ability to generate COS cells that support HL-60 cell adhesion. DNA sequencing positively identified one of these clones as encoding for ELAM-1 (Bevilacqua, M. P., et al., Science, (1989) 243:1160; Polte, T., et al., Nucleic Acids Res. (1990) 18:1083; Hession, C., et al., Proc. Natl. Acad. Sci. USA (1990) 87:1673). These publications are incorporated herein by reference for their disclosure of ELAM-1 and genetic material coding for its production. The complete nucleotide sequence of the ELAM-1 cDNA and predicted amino acid sequence of the ELAM-1 protein are given in the above cited article by Bevilacqua et al., which DNA and amino acid sequences are incorporated herein by reference (see also published PCT patent application WO90/13300 which was published Nov. 15, 1990, which is incorporated herein by reference).

A full length cDNA encoding ELAM-1 was obtained by 35 cycles of the polymerase chain reaction with 1 µg of total RNA extracted from IL-1 stimulated human umbilical vein endothelial cells, utilizing primers complementary to the untranslated flanking sequences SEQ ID NO:6 and SEQ ID NO:7. The 2 Kb insert generated was gel purified, directionally cloned into the mammalian expression vector, CDM8 that had been modified by the insertion of a SalI site into the polylinker, and grown in E. coli (MC1061/p3). Plasmids were isolated from individual colonies and used to transfect COS cells. Putative E-SELECTIN encoding plasmids were selected based on the ability of these transfected COS cells to support HL-60 cell adhesion 72 h posttransfection.

A positive cDNA whose sequence corresponded to the published sequence of E-SELECTIN with two nucleic acid substitutions was used in all experiments. COS cells were transfected with 1 µg of this plasmid DNA per $3.5–5.0 \times 10^5$ cells, with 400 µg/ml DEAE-dextran and 100 µM chloroquine for 4 h, followed by a brief exposure to 10% DMSO in PBS. Cells were metabolically radiolabeled overnight with carrier free $^{32}PO_4$ and harvested in PBS supplemented with 0.02% azide and 2 mM EDTA at 72 h posttransfection for use in cell adhesion studies.

Similarly, COS cells may be transfected with cDNAs that encode L-SELECTIN and/or P-SELECTIN. The production and characterization of L-SELECTIN IgG chimera constructs have been previously described by Watson S. R. et al., (1990) J. Cell Biol. 110:2221–2229. This chimera contains two complement binding domains, consistent with its natural expression. See Watson S. R. et al., (1991) J. Cell Biol. 115:235–243. P-SELECTIN chimera was constructed in a similar manner as described by Walz, G., et al (1990) Science 250, 1132–1135, and Aruffo, A. et al.(1991) Cell, 67, 35–44, respectively. The chimeras may be expressed in a suitable host cell, for example, 293 cells and purified. Protein A affinity chromatography is the preferred method of purification. E-SELECTIN and P-SELECTIN may be constructed with truncated complement binding domains to standardize the size of the chimeras and to facilitate their secretion. A variation of the above assay is to genetically engineer cells to express high levels of L-SELECTIN, E-SELECTIN, or P-SELECTIN on their surface, and to use the cells in lieu of purified selectin. Radiolabeled COS cells have been used in this type of assay, and can be transfected with cDNA that encodes for L-SELECTIN, E-SELECTIN or P-SELECTIN. After the cells have had a sufficient time to adhere to the ligand coated microtiter well, non-adherent cells are removed and the number of adherent cells determined. The number of adherent cells reflects the capacity of the ligand to bind to the selectin. The capacity of a particular peptide to interfere with selectin ligand binding is measured by running the assay in the presence of peptide. Thus, any candidate peptide of formula 1 may be verified to interfere with selectin ligand binding by a positive result in the foregoing assays. These assays provide a simple screen for determining the relative effectiveness of the various members of the group consisting of compounds of formula 1.

Non-therapeutic Uses of Peptides

In addition to their use in treating or preventing inflammation as is further described herein below, the peptides of formula 1 are useful in diagnostic and preparatory procedures both in vitro and in vivo. The peptides of formula 1 are as follows:

SEQ ID NO:1 wherein X is an aromatic amino acid, and n is 1, 2, or 3; X' is either a non-polar or polar uncharged amino acid, and n' is 1, 2, or 3; X" is a basic amino acid, and n" is 1 or 2.

Embodiments of the peptides of formula 1 include the following peptides.

SEQ ID NO:2

SEQ ID NO:3

SEQ ID NO:4, or

SEQ ID NO:5

The peptides may be acetylated at the amino terminal end and/or amidated at the carboxyl terminal end. Alternatively, pharmaceutically acceptable salt forms of the peptides may be made using methods known in the art.

Peptides may be conjugated to solid substrates and used for the purification of selectin receptor protein from biological samples. This is conducted most conveniently by arranging the coupled substrate as an affinity chromatography column and applying a sample putatively containing the selectin receptor protein to the affinity column under conditions wherein the selectin receptor protein is adsorbed whereas contaminating materials are not. The selectin receptor protein is then subsequently eluted, for example, by adjusting the eluent solution to containing competing amounts of the peptides of formulas 1–5 or by adjusting pH or salt parameters. Techniques for affinity purification are well understood, and routine optimization experiments will generate the appropriate conditions for conduct of the procedure.

The peptides may also be useful as detection reagents to determine the presence or absence of selectin or related carbohydrate-binding receptor ligands. For use in such diagnostic assays, a biological sample suspected to contain selectin receptor protein or a receptor protein closely related thereto is treated with a peptide of formulas 1–5 under conditions wherein complexation occurs between the receptor protein and the peptide, and the formation of the complex is detected. A wide variety of protocols may be utilized in such procedures, analogous to protocols applied in immunoassays. Thus, direct assay wherein the amount of complex formed is directly measured may be utilized; alternatively, competition assays may be used wherein labeled selectin receptor protein is supplied along with, and in competition with, the biological sample. In some forms of the assay, it is convenient to supply the peptides in labeled form so that the complex is detected directly; in alternate procedures, the complex may be detected by size separations, secondary labeling reagents, or other alternate means. Suitable labels are known in the art, and include radioactive labels, fluorescent labels, enzyme labels, chromogenic labels, or composites of these approaches.

The peptides may also be used as competitive diagnostic reagents to detect the quantity of selectin receptor*binding components, such as surface ligands, in biological fluids. For the conduct of such assays, the peptides of formula 1 are labeled as described above and mixed with the biological sample and contacted with the appropriate receptor protein; the diminution of binding of the labeled peptide to selectin receptor in the presence of biological sample is then determined.

The peptides may also be used in imagining studies in vivo. For use in such assays, the peptides are supplied with labels which can be detected by in vivo imaging techniques, such as scintigraphic labels including indium 111, technetium 99, iodine 131, and the like.

Techniques for coupling peptides to labels, including radiolabels for imaging, chromatographic supports, or other moieties useful in employing the peptides in the relevant procedures are well understood in the art.

Antibodies may also be prepared to the peptides by coupling these peptides to suitable carriers and administering the coupled materials to mammalian or other vertebrate subjects in standard immunization protocols with proper inclusion of adjuvants. Suitable immunogenic carriers include, for example, Keyhole Limpet Hemocyanin (KLH), tetanus toxoid, various serum albumins such as bovine serum albumin (BSA) and certain viral proteins such as rotaviral VP6 protein. These coupled materials are then administered in repeated injections to subjects such as rabbits, rats or mice and antibody titers monitored by standard immunoassay techniques. The resulting antisera may be used per se or the antibody-secreting cells generated by the immunization may be immortalized using standard techniques and used as a source of monoclonal preparations which are immunoreactive with the peptides. The resulting antibodies are useful in assay systems for determining the presence and/or amount of the relevant formula 1 peptide. Such assays are useful in monitoring the circulating levels of peptides in therapeutic treatments such as those described below.

It is important to note that antibody that binds to the peptides of formulas 1–5 would also have significant therapeutic applications. Such antibody would have the capacity to bind to P-selectin, E-selectin or L-selectin and interfere with binding of the selectins to the relevant ligand. This, in turn, would prevent or interfere with cell-cell adhesion of defined cell types which would have important medical applications.

Methods to conjugate peptides to carriers are known in the art; the hydroxyl groups of the present compounds provide functional groups which permit the employment of, for example, homo- or heterobifunctional linkers such as those marketed by Pierce Chemical Company, Rockford, Ill. Certain covalent linkers are described in U.S. Pat. No. 4,954,637.

Murine or human monoclonal preparations can be obtained by in vivo or in vitro immortalization of peripheral blood lymphocytes or spleen cells of animals using methods well known in the art, such as fusion with immortalizing cells as described by Kohler and Millstein 1975, Nature, 256:495; and Fendly, et al., 1987, Hybridoma, 6:359. In vitro techniques are generally described by Luben, R. and Mohler, M., 1980, Molecular Immunology, 17:635; Reading, C. Methods in Enzymology, 121 (Part One):18; or Voss, B.,1986, Methods in Enzymology, 121:27. Recombinant and/or humanized antibody may also be generated using methods known in the art.

Administration Protocols

The peptides of the invention are administered to a subject in need thereof for preventing or treating disease. Thus, the instant peptides may be utilized prophylactically or therapeutically. It must be noted that as used in this specification and the appended claims, "disease" refers to infectious (i.e. bacterial, viral etc infections) and non-infectious disease (i.e. cancer). Intended to come within the definition of infectious disease are inflammatory reactions that are a consequence of the initial infection, or complications thereof including sepsis.

Animal model systems are available to test the effectiveness of the peptides for treating or preventing disease, and such model systems are well known to the skilled practitioners of this art. For example, the beneficial effect of the invention peptides for treating or preventing sepsis can be demonstrated in one of several animal model systems. The preferred animal model system is baboon, and is described by Taylor, et al., 1987, *J. of Clinical Inv.*, 79:918, and by Taylor, et al., 1988, *Circulatory Shock.*, 26:227. A baboons response to bacterial exposure that causes sepsis is similar to that displayed by humans, as is the manner of response to therapeutic/prophylactic treatment. Thus, the efficacy of a particular treatment in baboons is predictive of how a human will respond.

The peptides are preferably administered with a pharmaceutically acceptable carrier, the nature of the carrier differing with the mode of administration, for example, oral administration, usually using a solid carrier and I.V. administration using a liquid salt solution carrier. Typically, injectable compositions are prepared as liquid solutions or suspensions; solid forms suitable for solution in, or suspension in, liquid vehicles prior to injection may also be prepared. The peptides may also be emulsified or the active ingredient encapsulated in liposome vehicles.

Suitable vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, for example, *Remington's Pharmaceutical Sciences*, Mack Publishing Company, Easton, Pa., 17th edition, 1985. Formulations may employ a variety of excipients including, for example, pharmaceutical grades of mannitol, lactose, starch, magnesium stearate, sodium saccharin cellulose, magnesium carbonate, and the like. Oral compositions may be taken in the form of solutions, suspensions, tablets, pills, capsules, sustained release formulations, or powders. Particularly useful is the administration of the subject ligand molecules directly in transdermal formulations with permeation enhancers such as DMSO. Other topical formulations can be administered to treat dermal inflammation. In addition, transmucosal administration may be effected using penetrants such as bile salts or fusidic acid derivatives optionally in combination with additional detergent molecules. These formulations are useful in the preparation of suppositories, for example, or nasal sprays. For suppositories, the vehicle composition will include traditional binders and carriers, such as polyalkylene glycols, or triglycerides. Such suppositories may be formed from mixtures containing the active ingredient in the range of about 0.5% to about 10% (w/w), preferably about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Typically, the compositions of the instant invention will contain from less than 1% to about 95% of the active ingredient, preferably about 10% to about 50%. Preferably, between about 10 mg and 50 mg will be administered to a child and between about 50 mg and 1000 mg will be administered to an adult. The frequency of administration will be determined by the care given based on patient responsiveness. Other effective dosages can be readily determined by one of ordinary skill in the art through routine trials establishing dose response curves.

In determining the dose to be administered, it will be noted that it may not be desirable to completely block all selectin receptors of a particular type. In order for a normal healing process to proceed, at least some of the white blood cells or neutrophils must be brought into the tissue in the areas where any wound, infection or disease state is occurring. The amount of peptide administered as blocking agents must be adjusted carefully based on the particular needs of the patient while taking into consideration a variety of factors such as the type of disease that is being treated.

The peptides may also be incorporated into liposomes or microspheres for administration. Methods for preparing both compositions are known in the art. For instance, U.S. Pat. No. 4,789,734 describes methods for encapsulating biological materials in liposomes. Microspheres can be made that contain peptides and that gradually release the peptides over time in a slow release mode. U.S. Pat. Nos. 4,906,474, 4,925,673 and 3,625,214.

The peptides of the present invention are useful to treat a wide range of diseases, for example autoimmune diseases such as rheumatoid arthritis and multiple sclerosis. The compositions of the invention are applicable to treat any disease state wherein the immune system turns against the body causing the white cells to accumulate in the tissues to the extent that they cause tissue damage, swelling, inflammation and/or pain.

Reperfusion injury is a major problem in clinical cardiology. Therapeutic agents that reduce leukocyte adherence in ischemic myocardium can significantly enhance the therapeutic efficacy of thrombolytic agents. Thrombolytic therapy with agents such as tissue plasminogen activator or streptokinase can relieve coronary artery obstruction in many patients with severe myocardial ischemia prior to irreversible myocardial cell death. However, many such patients still suffer myocardial neurosis despite restoration of blood flow. This "reperfusion injury" is known to be associated with adherence of leukocytes to vascular endothelium in the ischemic zone, presumably in part because of activation of platelets and endothelium by thrombin and cytokines that makes them adhesive for leukocytes (Romson et al., Circulation 67:1016–1023, 1983). These adherent leukocytes can migrate through the endothelium and estray ischemic myocardium just as it is being rescued by restoration of blood flow.

There are a number of other common clinical disorders in which ischemia and reperfusion results in organ injury mediated by adherence of leukocytes to vascular surfaces, including strokes; mesenteric and peripheral vascular disease; organ transplantation; and circulatory shock (in this case many organs might be damaged following restoration of blood flow).

Formulations of the present invention might also be administered to prevent the undesirable after effects of tissue damage resulting from heart attacks. When a heart attack occurs and the patient has been revived, such as by the application of anticoagulants or thrombolytic (e.g., tPA), the endothelial lining where a clot was formed has often suffered damage. When the antithrombotic has removed the clot, the damaged tissue beneath the clot and other damaged tissue in the endothelial lining which has been deprived of oxygen become activated. The activated endothelial cells then synthesize selectin receptors, for example ELAM-1 receptors, within hours of the cells being damaged. The receptors are extended into the blood vessels where they adhere to glycoconjugate ligand molecules on the surface of white blood cells. Large numbers of white blood cells are quickly captured and brought into the tissue surrounding the area of activated endothelial cells, resulting in inflammation, swelling and necrosis which thereby decreases the likelihood of survival of the patient.

In addition to treating patients suffering from the trauma resulting from heart attack, patients suffering from actual physical trauma could be treated with formulations of the invention in order to relieve the amount of inflammation and swelling which normally result after an area of the body is subjected to severe trauma. Other conditions treatable using formulations of the invention include various types of arthritis and adult respiratory distress syndrome. After reading the present disclosure, those skilled in the art will recognize other disease states and/or symptoms which might be treated and/or mitigated by the administration of formulations of the present invention.

It is important to note that the half-lives of the instant peptides in vivo can be increased if desired using methods known to those skilled in this art. Such methods are described in U.S. Pat. No. 4,629,784. Thus, in those instance when it is desirable to increase the circulation time of a peptide it can be modified using the aforementioned methods.

The following examples are intended to illustrate but not to limit the invention.

EXAMPLE 1

Inhibitory Peptide Binding Assay

The embodiment peptide, SEQ ID NO:2, acetylated at its amino terminus and/or amidated at its carboxyl terminus, was assayed for selectin ligand inhibitory binding activity as follows.

Preparation of Selectins 0.625 ug of either P or E-selectin in 75 ul of 50 mM carbonate buffer, pH 9.5, was added to wells of a black microfluor plate. The selectins were incubated overnight at 4° C. to permit maximal binding of the relevant selectin to the wells. The carbonate buffer was aspirated from the wells to remove any unbound selectin chimera. Next, 100 ul of 5% BSA in PBS was added to all wells containing chimera, and the plate allowed to stand at room temperature for 60 minutes to permit BSA sufficient time to block the wells. Just prior to the addition of the labeled cell suspension, prepared as set forth below, the BSA was aspirated from the wells.

Preparation of Cells

HL-60 Cells were used in the assay. About $1.5 \times 10^7$ cells were washed free of culture medium with Dulbecco's PBS with calcium and magnesium, and the cells suspended in 5 ml of PBS. 5 ul of 10 mM BCECF-AM in DMSO was added, and the cell suspension incubated at 37° C. for 40 minutes, after which the cells were washed free of unincorporated label using PBS. Finally, cell density was adjusted to $3.0 \times 10^6$ cells/ml in PBS.

Preparation of Peptide

A stock peptide solution was made up as follows. 7.47 mg [Mr 1138.6] of peptide was dissolved in 1000 ul of Dulbecco's PBS with calcium and magnesium, and the solution centrifuged to remove any particulate material. The supernatant was removed and the concentration of peptide determined by amino acid analysis. The peptide concentration was 949 uM. The solution was two-fold serially diluted with PBS to give peptide concentrations of 828, 414, 207, 103.5, 51.8, 25.9, 12.9, and 6.47 uM.

Cell-Selection Adhesion Assay

Using the HL-60 cells and reagents prepared above, the capacity of the peptide to inhibit HL-60 cell binding to either P or E-selectin was determined as follows. 125 ul of the labeled cell suspension was added to 250 ul of each of the eight peptide concentrations to give final peptide concentrations of 552, 276, 138, 69, 34.5, 17.25, 8.63, and 4.31 uM. 500 ul of the labeled cell suspension was added to 1000 ul of PBS and used in control and non-specific fluorescence wells.

75 ul of each mixture, either control or peptide mixture, were transferred to wells of the microfluor plate, and incubated at 37° C. for 1 hour. At the end of this period unbound cells were aspirated from all wells.

Background fluorescence was controlled for using an equivalent number of unlabelled cells.

Next, to solubilize the cells, 2% Triton X-100 in 0.1M tris buffer (pH 9.5) was added to all wells of the microfluor plate to a final volume of 75 ul. After allowing the plate to stand at room temperature for 1 hour, the fluorescence at 538 nm was recorded in each well using a microplate fluorometer. The samples were excited at 485 nm.

Figure 1:
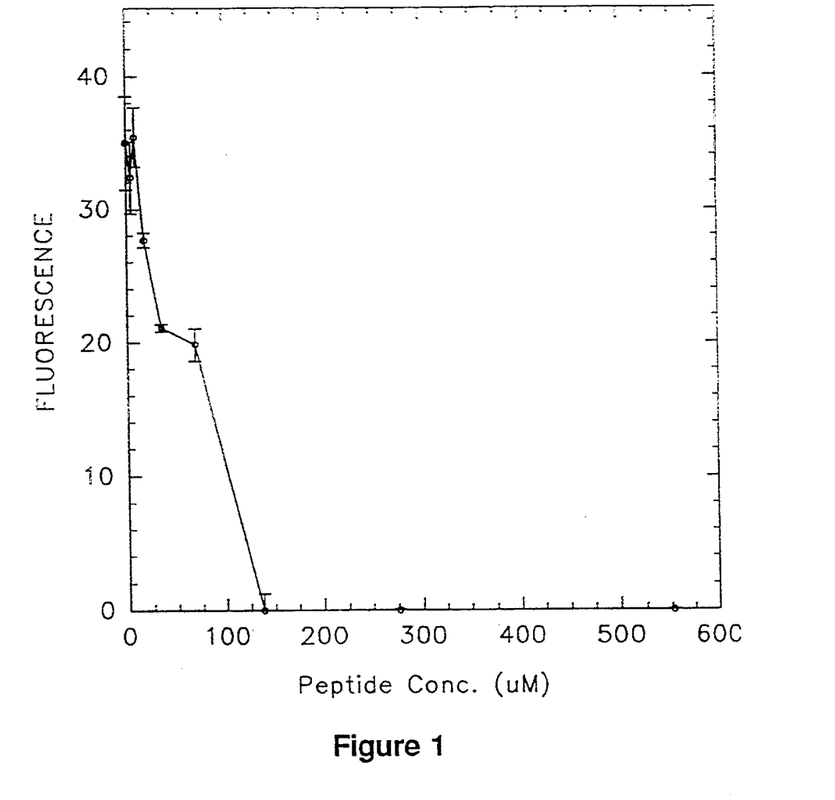
FIG. 1 shows the effects of the peptide SEQ ID NO:2, acetylated at its amino terminus and amidated at its carboxyl terminus, on HL-60 cell binding to P-selectin.
Figure 2:
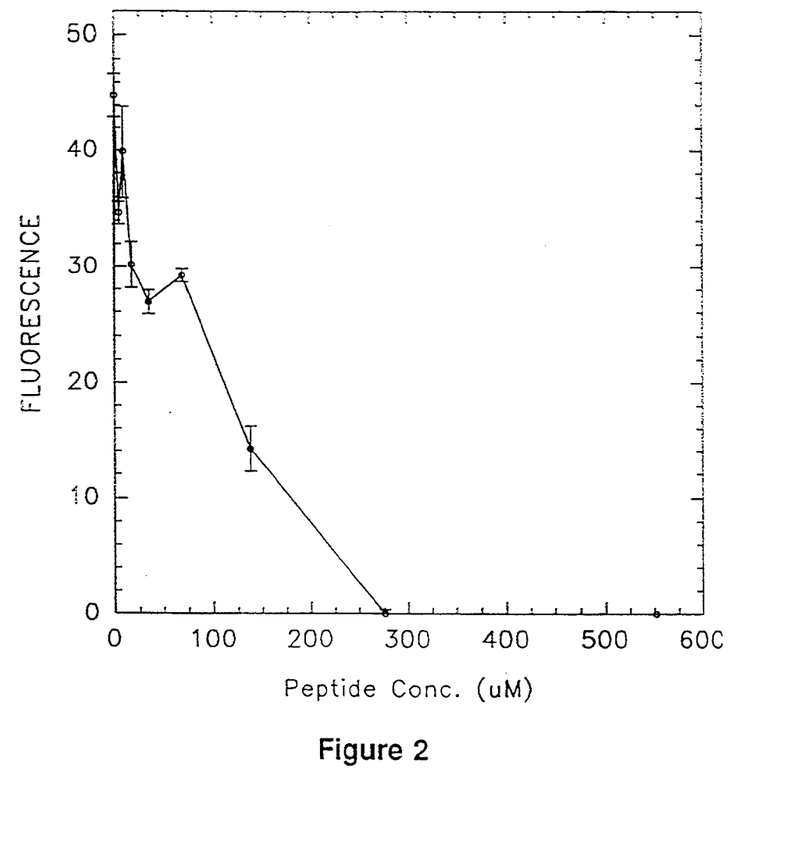
FIG. 2 shows the effects of the peptide SEQ ID NO:2, acetylated at its amino terminus and amidated at its carboxyl terminus, on HL-60 cell binding to E-selectin.

The results are shown in FIGS. 1 and 2 for peptide that is both acetylated at its amino terminus and amidated at its carboxyl terminus. It is apparent from FIG. 1 that the $IC_{50}$ for P-selectin binding is about 77.5 uM. In contrast, FIG. 2 shows that the $IC_{50}$ for E-selectin binding it is about 102 uM. IC$_{50}$ was the peptide concentration that gave half maximal fluorescence.

EXAMPLE 2

Prevention or Treatment of Sepsis

The effectiveness of the embodiment peptide, SEQ ID NO:2, acetylated at its amino terminus and/or amidated at its carboxyl terminus would be shown to be useful to treat or prevent sepsis in a baboon sepsis model system as described by Taylor, et al., 1987, *J. of Clinical. Inv.*, 79:918, and by Taylor, et al., 1988, *Circulatory Shock*, 26:227. Briefly, this would consists of determining if the peptide is effective in treating sepsis by preventing the death, or prolonging the lives of septic animals to either a lethal or sublethal dose of *E. coli*. A lethal or sublethal dose of *E. coli* consist of approximately $4 \times 10^{10}$ and $0.4 \times 10^{10}$ organisms, respectively. Baboons that receive a lethal dose of *E. coli* invariably die within 16-32 hours. Taylor, et al., 1987, *J. of Clinical Inv.*, 79:918, and Taylor, et al., 1988, *Circulatory Shock*, 26:227.

The effectiveness of the peptide in preventing the death or prolonging the lives of baboons would be tested using two administration routines wherein the peptide is delivered in physiological saline. In the first, between 1 and 10 mg of peptide per kg of body weight is administered in three separate doses at 24, 22, and 21 hours before a lethal challenge of bacteria. Alternatively, a similar dose of *E. coli* can be administered in a single dose simultaneously with the bacterial challenge. In both instances the peptide would considerably extend the lifetime of the baboons that receive the multiple or single dose treatment and survive well beyond 48 hours.

EXAMPLE 3

Prevention or Treatment of Peritonitis

Certain of the invention peptides were shown to be efficacious in preventing peritonitis. The most efficacious peptides were SEQ ID NO:2, acetylated at its amino terminus, SEQ ID NO:3 and SEQ ID NO:5. The experiments were conducted using a murine thioglycollate induced peritonitis model. The assay materials and methods are generally described by Lewinsohn, D. et al., *J. Immun.*, (1987) 138:4313-4321, or Watson, S. et al., *Nature* (1991) 349:164-166.

This assay measures the ability of the peptides to inhibit neutrophil migration to the peritoneal cavity, the migration being initiated by the presence of thioglycollate in the peritoneal cavity. Thioglycollate is a known and effective inflammatory agent that causes neutrophil migration into the mouse peritoneum when it is administered intraperitoneally. Lewinsohn, D. et al., *J. Immun.* (1987) 138:4313-4321.

Briefly, female Swiss Webster mice weighing about 25 grams were injected in the tail vein in 200 ul of phosphate buffered saline (PBS) with or without the appropriate peptide. Peptides were prepared as described in Example 1 with the addition of a 30 minute incubation period at 37° C. to allow the peptides to solubilize before centrifugation. The pH of the peptide solutions was adjusted to neutrality by the addition of either NaOH or HCL and sterilized by filtration through a 0.2u filter. Peptide concentrations were determined either by absorbance at 275 nm, using empirically determined molar extinction coefficients for each peptide, or by amino acid compositional analysis. The extinction coefficients are shown in Table 1.

TABLE 1

| Extinction Coefficients For Synthetic Peptides | | | |
|---|---|---|---|
| AMINO ACID SEQUENCE* | ABS. (275 NM) | PEPTIDE CONC. (Mm) | $\epsilon_{275}$ (Mm$^{-1}$) |
| SEQ ID NO:2 | 1.825 | 1.29 mM | 1.415 |
| (Ac) SEQ ID NO:2 | 1.978 | 1.16 mM | 1.698 |
| SEQ ID NO:4 | 1.816 | 6.18 mM | 0.294 |
| SEQ ID NO:8 | 1.857 | 2.89 mM | 0.643 |
| SEQ ID NO:9 | | | |
| SEQ ID NO:3 | 1.912 | 6.42 mM | 0.298 |
| SEQ ID NO:5 | 1.797 | 2.49 Mm | 0.722 |
| SEQ ID NO:10 | 1.743 | 2.60 mM | 0.670 |
| SEQ ID NO:11** | | | |

*the amino and carboxyl terminal ends of the peptides, by convention, are at the left and right hand sides of the peptides, respectively.
**The concentrations of these peptides were determined by amino acid analysis.

Immediately following injection with peptide or PBS, the mice were injected intraperitoneally with 1 ml of thioglycollate medium prepared as described by the manufacturer, BBL. Three hours following injection of the thioglycollate solution the mice were sacrificed by $CO_2$ asphyxiation, and the number of cells in the peritoneum removed by lavage with 5 ml of heparinized (5U/ml) 0.9% sodium chloride containing 0.1% bovine serum albumin. Cell number was determined using a Coulter Counter. The cells were prepared for counting by diluting the lavage fluid with 1:50 in a commercial physiological isotonic solution, Isoton II, and the cells lysed by adding S/P Lysing and Hemoglobin Reagent obtained from Baxter Diagnostics, Inc. (1:100 final dilution). Cell nuclei were counted in a sized window with lower and upper limits set at 3.9 and 5.7 um, respectively.

Table 2 shows the number of cells in the peritoneal cavity from mice injected with PBS or PBS containing peptide. The amount of peptide injected per kilogram of mouse body weight is also shown in the table. All the peptides tested; SEQ ID NO:2, acetylated at its amino terminus, SEQ ID NO:3, SEQ ID NO:4, and SEQ ID NO:5 exhibited substantial inhibitory activity as revealed by fewer cells in the peritoneal cavity compared to the PBS control. The most efficacious peptides were SEQ ID NO:2, acetylated at its amino terminus, SEQ ID NO:3 and SEQ ID NO:5.

TABLE 2

| Inhibition of Thioglycolate Induced Peritonitis by Selectin Peptides | | |
|---|---|---|
| | | Percent Inhibition |
| STRUCTURE* | Peptide Dose mg/kg | Expt 1 | Expt 2 |
| (Ac)SEQ ID NO:2 | 12 | 31 | |
| SEQ ID NO:3 | 15 | 71 | 50 |
| SEQ ID NO:3 | 37 | | 66 |
| SEQ ID NO:5 | 16 | | 71 |

*the amino and carboxyl terminal ends of the peptides, by convention, are at the left and right hand sides of the peptides, respectively.

Neutrophil-mediated inflammation has been shown to be directly involved in certain human diseases. Examples would include peritonitis as set forth above, adult respiratory distress syndrome, and reperfusion injury. Neutrophils exert this effect by adhesive interactions between neutrophils and the endothelium which facilitates extravasation of the neutrophils to the site of inflammation. Compounds that inhibit neutrophil extravasation will have significant medical uses. Thus, considering the reduction in neutrophils in the peritoneal cavity compared to the PBS control in the above experiments, it can be concluded that the peptides of the instant invention will have widespread medical applications for diseases that have an inflammatory component.

EXAMPLE 4

Inhibition of HUVEC Cell Binding to HL-60 Cells

A well known property of cancer cells is the capacity to spread throughout the body from their site of origin, a process termed metastasis. The process involves extravasation from the primary tumor site into the blood, and subsequent extravasation out of the blood. Thus, it would be possible to prevent or eliminate metastasis if extravasation of cancer cell could be controlled. The following experiment shows that the peptides of the instant invention prevent adhesion of human cancer cells, HL-60 cells, to human endothelial cells, and thus would have applications for the treatment or prevention of metastatic cancer. This establishes yet another clear medical utility for the peptides.

Human umbilical vein endothelial cells (HUVEC) were cultured in endothelial cell culture, CS-C-500, serum containing medium. HL-60 cells were grown in RPMI medium containing 10% fetal calf serum. HUVEC cells were prepared for the cell adhesion assay by seeding $10^4$ cells/well in 96 well microtiter plates on Type 5 collagen. The cells were allowed to reach confluence (3-4 days growth) and then stimulated to express E-selectin by incubating the cells with 5 ng of recombinant interleukin-1 beta at 37° C. for 4-6 hours. Control cells were incubated with growth medium alone. HL-60 cells were washed three times with phosphate buffered saline (PBS) containing 1% bovine serum albumin (BSA) and incubated with the appropriate peptide at 4° C. for 30 minutes. The peptide-HL-60 mixture was transferred to the wells containing HUVECs and incubated for 15 minutes at 4° C. The wells were washed twice with PBS and 100 μl of RPMI medium and the plate was frozen at −20° C. and thawed. The level of myeloperoxidase activity in the lysed cells was measured by adding a solution of O-dianisidine/hydrogen peroxide in 0.01M potassium phosphate buffer, pH 6.0 and incubating the wells at room temperature. Product formation was measured at 450 nm. See, Bevilaqua, M. et al., *J. Clin. Invest.* 76:2003–2008.

Table 2 presents the results of 3 experiments and the data are expressed in the form of the concentration of the peptides that inhibit by 50% ($IC_{50}$) the binding of cancer cells to endothelial cells, that is, HL-60 cells to umbilical vein endothelial cells. It is immediately apparent upon reviewing the data that many of the peptides effectively block HL-60 cell binding. The most efficacious are SEQ ID NO:2, (Ac)SEQ ID NO:2, SEQ ID NO:3, SEQ ID NO:5. These data clearly establish that the peptides of the invention will have significant medical applications for the treatment or prevention of cancer.

TABLE 3

Inhibition of HUVEC/HL-60 Cell Binding by Selectin Peptides

| STRUCTURE* | Expt 1 $IC_{50}$ (μM) | Expt 2 $IC_{50}$ (μM) | Expt 3 $IC_{50}$ (μM) |
|---|---|---|---|
| SEQ ID NO:2 |  | 25 | 25 |
| (Ac)SEQ ID NO:2 |  | 20 | 30 |
| YWIGIRK |  | 70 | 300 |
| WIGIRK | 400 | 1000 | 1000 |
| IGIRK |  |  | 2000 |
| YYWIGIR | 3 | 20 | 7 |
| YWIGIR | 20 | 50 | 10 |
| WIGIR |  | 400 | >1000 |
| IGIR |  | 6000 | >6000 |

*the amino and carboxyl terminal ends of the peptides, by convention, are at the left and right hand sides of the peptides, respectively.

It will be appreciated by skilled practitioners in this art, that while the metes and bounds of the invention are as set forth in the following claims, there exists numerous equivalent materials and methods which would substitute for those described and claimed herein, and thus fall within the scope of the claims.

What is claimed is:

1. A peptide selected from the group consisting of NH₂YYWIGIRCOOH, NH₂YWIGIRKCOOH, NH₂YWIGIRCOOH and NH₂YYWIGIRKCOOH.

2. A peptide as described in claim 1 in said amino terminus is acetylated.

3. A peptide as described in claim 2 wherein said carboxyl group is amidated.

4. A peptide as described in claim 3 wherein said carboxyl group is amidated and said amino terminus is acetylated.

5. The peptide SEQ ID NO:3, wherein said peptide carboxyl group may be amidated or said amino terminus acetylated and said carboxyl group is amidated.

6. The peptide SEQ ID NO:4, wherein said peptide carboxyl group may be amidated or said amino terminus acetylated and said carboxyl group is amidated.

7. The peptide SEQ ID NO:5, wherein said peptide carboxyl group may be amidated or said amino terminus acetylated and said carboxyl group is amidated.

8. The peptide SEQ ID NO:2, wherein said peptide carboxyl group may be amidated or said amino terminus acetylated and said carboxyl group is amidated.

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear     ( i i ) MOLECULE TYPE: peptide ( i x ) FEATURE:
    ( A ) NAME/KEY: Peptide
    ( B ) LOCATION: 1..2
    ( D ) OTHER INFORMATION: /label=X
        / note="X is an aromatic amino acid"

( i x ) FEATURE:
    ( A ) NAME/KEY: Peptide
    ( B ) LOCATION: 2..3
    ( D ) OTHER INFORMATION: /label=x
        / note="x is 1, 2, or 3"

( i x ) FEATURE:
    ( A ) NAME/KEY: Peptide
    ( B ) LOCATION: 3..4
    ( D ) OTHER INFORMATION: /label=X'
        / note="X'is a non-polar amino acid"

( i x ) FEATURE:
    ( A ) NAME/KEY: Peptide
    ( B ) LOCATION: 4..5
    ( D ) OTHER INFORMATION: /label=x'
        / note="x'is 1, 2, or 3"

( i x ) FEATURE:
    ( A ) NAME/KEY: Peptide
    ( B ) LOCATION: 5..6
    ( D ) OTHER INFORMATION: /label=X"
        / note="X"is a polar amino acid"

( i x ) FEATURE:
    ( A ) NAME/KEY: Peptide
    ( B ) LOCATION: 6
    ( D ) OTHER INFORMATION: /label=x"
        / note="x"is 1 or 2"

( x i ) SEQUENCE DESCRIPTION: SEQ ID NO:1:

Xaa Xaa Xaa Xaa Xaa Xaa
1                   5

( 2 ) INFORMATION FOR SEQ ID NO:2:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:2:

Tyr Tyr Trp Ile Gly Ile Arg Lys
1                   5

( 2 ) INFORMATION FOR SEQ ID NO:3:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:3:

Tyr Tyr Trp Ile Gly Ile Arg
1                   5

( 2 ) INFORMATION FOR SEQ ID NO:4:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

Tyr Trp Ile Gly Ile Arg Lys
1               5

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:5:

Tyr Trp Ile Gly Ile Arg
1               5

( 2 ) INFORMATION FOR SEQ ID NO:6:

( i ) SEQUENCE CHARACTERISTICS:
        ( A ) LENGTH: 31 base pairs
        ( B ) TYPE: nucleic acid
        ( C ) STRANDEDNESS: double
        ( D ) TOPOLOGY: linear     ( i i ) MOLECULE TYPE: cDNA     ( x i ) SEQUENCE DESCRIPTION: SEQ ID NO:6:

GGTGCGGCCG CGGCCAGAGA CCCGAGGAGA G        31

( 2 ) INFORMATION FOR SEQ ID NO:7:

( i ) SEQUENCE CHARACTERISTICS:
        ( A ) LENGTH: 29 base pairs
        ( B ) TYPE: nucleic acid
        ( C ) STRANDEDNESS: double
        ( D ) TOPOLOGY: linear     ( i i ) MOLECULE TYPE: cDNA     ( x i ) SEQUENCE DESCRIPTION: SEQ ID NO:7:

GGTGTCGACC CCACCTGAGA GATCCTGTG        29

( 2 ) INFORMATION FOR SEQ ID NO:8:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:8:

Trp Ile Gly Ile Arg Lys
1               5

( 2 ) INFORMATION FOR SEQ ID NO:9:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:9:

Ile Gly Ile Arg Lys
1                 5

(2) INFORMATION FOR SEQ ID NO:10:

(i) SEQUENCE CHARACTERISTICS:
        (A) LENGTH: 5 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO:10:

Trp Ile Gly Ile Arg
1                 5

(2) INFORMATION FOR SEQ ID NO:11:

(i) SEQUENCE CHARACTERISTICS:
        (A) LENGTH: 4 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO:11:

Ile Gly Ile Arg
1

* * * * *